(12) United States Patent
Beck

(10) Patent No.: US 8,911,414 B2
(45) Date of Patent: Dec. 16, 2014

(54) ANTI FREE-FLOW OCCLUDER AND PRIMING ACTUATOR PAD

(75) Inventor: Kent Beck, Layton, UT (US)

(73) Assignee: Zevex, Inc., Salt Lake City, UT (US)

(*) Notice: Subject to any disclaimer, the term of this patent is extended or adjusted under 35 U.S.C. 154(b) by 442 days.

(21) Appl. No.: 13/248,596

(22) Filed: Sep. 29, 2011

(65) Prior Publication Data

US 2012/0083737 A1   Apr. 5, 2012

Related U.S. Application Data

(60) Provisional application No. 61/388,901, filed on Oct. 1, 2010.

(51) Int. Cl.
 *A61M 5/00* (2006.01)
 *A61M 5/142* (2006.01)
 *A61M 5/168* (2006.01)

(52) U.S. Cl.
 CPC ........ *A61M 5/14212* (2013.01); *A61M 5/14232* (2013.01); *A61M 5/16881* (2013.01)
 USPC .......................................................... 604/246

(58) Field of Classification Search
 USPC .................. 604/174–180, 246–250, 67
 See application file for complete search history.

(56) References Cited

U.S. PATENT DOCUMENTS

| 584,091 | A | 6/1897 | Leidich |
|---|---|---|---|
| 1,238,521 | A | 8/1917 | Janish, Jr. |
| 2,471,623 | A | 5/1949 | Hubbell |
| 2,518,165 | A | 8/1950 | Millard |
| 2,858,095 | A | 10/1958 | Harris et al. |
| 2,899,907 | A | 8/1959 | Becher |
| 2,999,499 | A | 11/1961 | Willet |
| 3,213,882 | A | 10/1965 | Beatty |
| 3,329,391 | A | 7/1967 | Deane |
| D208,753 | S | 9/1967 | Curry |
| 3,497,175 | A | 2/1970 | Koland |
| 3,707,972 | A | 1/1973 | Villari et al. |
| 3,736,930 | A | 6/1973 | Georgi |
| 3,768,934 | A | 10/1973 | Magerle |
| 3,790,313 | A | 2/1974 | Magerle |

(Continued)

FOREIGN PATENT DOCUMENTS

| DE | 2447005 | 10/1974 |
|---|---|---|
| DE | 20000965 U1 | 1/2000 |

(Continued)

OTHER PUBLICATIONS

WIPO, Written Opinion of the International Searching Authority in International Application No. PCT/US2011/053955, mailed Apr. 26, 2012.

(Continued)

*Primary Examiner* — Nicholas Lucchesi
*Assistant Examiner* — Diva K Chander
(74) *Attorney, Agent, or Firm* — Hodgson Russ LLP

(57) ABSTRACT

A system for selectively preventing free flow in a tube includes an in-line occluder disposed in the tube and an actuator pad for creating a flow path between the tube and the occluder. The actuation pad presses towards the occluder from a single side and stretches the tube to create a large flow path. The occluder stem is strengthened to resist deformation and damage from the forces applied by the actuator pad.

24 Claims, 17 Drawing Sheets

(56) References Cited

U.S. PATENT DOCUMENTS

| | | | |
|---|---|---|---|
| 3,985,140 A | 10/1976 | Harris | |
| 3,998,364 A | 12/1976 | Hollander | |
| 4,037,596 A | 7/1977 | LeFevre et al. | |
| 4,063,555 A | 12/1977 | Ulinder | |
| 4,065,093 A | 12/1977 | Phillips | |
| 4,106,675 A | 8/1978 | Taylor | |
| 4,142,645 A | 3/1979 | Walton | |
| 4,160,383 A | 7/1979 | Rauschenberger | |
| 4,187,057 A | 2/1980 | Xanthopoulos | |
| 4,193,174 A * | 3/1980 | Stephens | 24/532 |
| 4,217,993 A | 8/1980 | Jess et al. | |
| 4,229,299 A | 10/1980 | Savitz et al. | |
| 4,230,151 A | 10/1980 | Jonsson | |
| 4,236,880 A | 12/1980 | Archibald | |
| 4,300,571 A | 11/1981 | Waldbillig | |
| 4,373,524 A | 2/1983 | Leibinsohn | |
| 4,381,591 A | 5/1983 | Barger et al. | |
| 4,382,453 A | 5/1983 | Bujan et al. | |
| 4,425,116 A | 1/1984 | Bilstad et al. | |
| 4,430,073 A | 2/1984 | Bemis et al. | |
| 4,447,191 A | 5/1984 | Bilstad et al. | |
| 4,453,295 A | 6/1984 | Laszczower | |
| 4,469,481 A | 9/1984 | Kobayashi | |
| 4,498,843 A | 2/1985 | Schneider et al. | |
| 4,524,802 A | 6/1985 | Lawrence et al. | |
| 4,527,588 A | 7/1985 | Tseo et al. | |
| 4,529,401 A | 7/1985 | Leslie et al. | |
| 4,559,036 A | 12/1985 | Wunsch | |
| 4,559,045 A | 12/1985 | Danby et al. | |
| 4,579,553 A | 4/1986 | Urquhart et al. | |
| D284,221 S | 6/1986 | Kerkut | |
| 4,596,557 A | 6/1986 | Pexa | |
| 4,601,700 A | 7/1986 | Thompson et al. | |
| 4,624,663 A | 11/1986 | Danby et al. | |
| 4,634,092 A | 1/1987 | Daniell et al. | |
| 4,645,489 A | 2/1987 | Krumme et al. | |
| 4,689,043 A * | 8/1987 | Bisha | 604/250 |
| 4,728,324 A | 3/1988 | Steigerwald et al. | |
| 4,730,635 A | 3/1988 | Linden | |
| 4,787,406 A | 11/1988 | Edwards et al. | |
| 4,850,807 A | 7/1989 | Frantz | |
| 4,857,818 A | 8/1989 | Hobbs | |
| 4,884,013 A | 11/1989 | Jackson et al. | |
| 4,910,682 A | 3/1990 | Wolff et al. | |
| 4,913,401 A | 4/1990 | Handke | |
| 4,913,703 A | 4/1990 | Pasqualucci | |
| 4,919,650 A | 4/1990 | Feingold et al. | |
| 4,932,629 A | 6/1990 | Rodomista et al. | |
| 4,932,938 A | 6/1990 | Goldberg et al. | |
| 4,935,010 A * | 6/1990 | Cox et al. | 604/122 |
| 4,944,485 A * | 7/1990 | Daoud et al. | 251/9 |
| 4,960,259 A | 10/1990 | Sunnanvader et al. | |
| 4,976,687 A | 12/1990 | Martin | |
| 5,017,192 A | 5/1991 | Dodge et al. | |
| 5,020,562 A | 6/1991 | Richmond et al. | |
| 5,022,422 A | 6/1991 | di Palma | |
| 5,029,621 A | 7/1991 | Lewis | |
| 5,083,561 A | 1/1992 | Russo | |
| 5,098,406 A | 3/1992 | Sawyer | |
| 5,099,184 A | 3/1992 | Hornung et al. | |
| 5,151,019 A | 9/1992 | Danby et al. | |
| 5,195,960 A | 3/1993 | Hossain et al. | |
| 5,201,711 A | 4/1993 | Pasqualucci | |
| 5,219,327 A | 6/1993 | Okada | |
| 5,232,193 A | 8/1993 | Skakoon | |
| 5,238,218 A | 8/1993 | Mackal | |
| 5,244,463 A | 9/1993 | Cordner, Jr. et al. | |
| 5,254,083 A | 10/1993 | Gentelia et al. | |
| 5,254,992 A | 10/1993 | Keen et al. | |
| 5,257,978 A | 11/1993 | Haber et al. | |
| 5,265,847 A | 11/1993 | Vorhis | |
| 5,279,556 A | 1/1994 | Goi et al. | |
| 5,312,334 A | 5/1994 | Hara et al. | |
| 5,336,174 A | 8/1994 | Daoud et al. | |
| 5,351,932 A | 10/1994 | Von Herrmann | |
| 5,355,735 A | 10/1994 | Miller et al. | |
| 5,370,612 A | 12/1994 | Maeda et al. | |
| 5,391,144 A | 2/1995 | Sakurai et al. | |
| 5,395,320 A | 3/1995 | Padda et al. | |
| 5,395,351 A | 3/1995 | Munsch | |
| 5,396,925 A | 3/1995 | Poli | |
| D357,312 S | 4/1995 | Riquier et al. | |
| 5,437,642 A * | 8/1995 | Thill et al. | 604/153 |
| 5,438,868 A | 8/1995 | Holden et al. | |
| 5,456,887 A | 10/1995 | Calvo et al. | |
| 5,474,544 A | 12/1995 | Lynn | |
| 5,482,446 A | 1/1996 | Williamson et al. | |
| 5,514,102 A | 5/1996 | Winterer et al. | |
| 5,531,680 A | 7/1996 | Dumas et al. | |
| 5,531,713 A | 7/1996 | Mastronardi et al. | |
| 5,538,405 A | 7/1996 | Patno et al. | |
| 5,556,386 A | 9/1996 | Todd | |
| D374,718 S | 10/1996 | Dodge et al. | |
| 5,575,631 A | 11/1996 | Jester | |
| 5,578,070 A | 11/1996 | Utterberg | |
| 5,599,315 A * | 2/1997 | McPhee | 604/218 |
| 5,630,710 A | 5/1997 | Tune et al. | |
| 5,657,000 A | 8/1997 | Ellingboe | |
| 5,683,233 A | 11/1997 | Moubayed et al. | |
| D388,876 S | 1/1998 | Sampson | |
| D389,228 S | 1/1998 | Winterer et al. | |
| 5,704,584 A | 1/1998 | Winterer et al. | |
| 5,720,721 A | 2/1998 | Dumas et al. | |
| 5,733,061 A | 3/1998 | Child | |
| 5,746,756 A | 5/1998 | Bromfield et al. | |
| 5,789,675 A | 8/1998 | Blaine et al. | |
| 5,791,881 A | 8/1998 | Moubayed et al. | |
| 5,800,405 A * | 9/1998 | McPhee | 604/218 |
| 5,807,312 A | 9/1998 | Dzwonkiewicz | |
| 5,810,323 A | 9/1998 | Winterer et al. | |
| 5,816,779 A * | 10/1998 | Lawless et al. | 417/63 |
| 5,826,621 A | 10/1998 | Jemmott | |
| 5,924,852 A | 7/1999 | Moubayed et al. | |
| 5,935,106 A | 8/1999 | Olsen | |
| 5,954,485 A * | 9/1999 | Johnson et al. | 417/474 |
| 5,971,357 A | 10/1999 | Denton et al. | |
| 5,996,650 A | 12/1999 | Phallen et al. | |
| 6,017,326 A | 1/2000 | Pasqualucci | |
| 6,017,332 A | 1/2000 | Urrutia | |
| 6,023,970 A | 2/2000 | Blaine | |
| 6,030,359 A | 2/2000 | Nowosielski | |
| 6,048,331 A | 4/2000 | Tsugita | |
| 6,059,753 A * | 5/2000 | Faust et al. | 604/131 |
| 6,092,695 A | 7/2000 | Loeffler | |
| 6,121,739 A | 9/2000 | Haberlander | |
| 6,142,979 A * | 11/2000 | McNally et al. | 604/246 |
| 6,164,921 A | 12/2000 | Moubayed et al. | |
| RE37,074 E | 2/2001 | Danby et al. | |
| 6,183,447 B1 | 2/2001 | Urrutia | |
| 6,192,752 B1 | 2/2001 | Blaine | |
| 6,196,922 B1 | 3/2001 | Hantschk et al. | |
| 6,196,992 B1 | 3/2001 | Keilman et al. | |
| 6,209,538 B1 | 4/2001 | Casper et al. | |
| 6,261,262 B1 | 7/2001 | Briggs et al. | |
| 6,328,720 B1 | 12/2001 | McNally et al. | |
| D455,489 S | 4/2002 | Beck et al. | |
| 6,371,732 B1 | 4/2002 | Moubayed et al. | |
| 6,398,758 B1 | 6/2002 | Jacobsen et al. | |
| 6,398,780 B1 | 6/2002 | Farley et al. | |
| 6,416,293 B1 | 7/2002 | Bouchard et al. | |
| 6,461,335 B1 | 10/2002 | Noecker | |
| 6,494,864 B1 | 12/2002 | Kerwin et al. | |
| 6,506,035 B1 | 1/2003 | Beck | |
| 6,523,414 B1 | 2/2003 | Malmstrom et al. | |
| 6,531,708 B1 * | 3/2003 | Malmstrom et al. | 250/573 |
| RE38,145 E | 6/2003 | Lynn | |
| 6,595,950 B1 | 7/2003 | Miles et al. | |
| 6,623,447 B2 | 9/2003 | Miles et al. | |
| 6,636,010 B1 | 10/2003 | Malmstrom et al. | |
| H2090 H | 11/2003 | Walker | |
| 6,659,976 B2 | 12/2003 | Beck et al. | |
| 6,682,500 B2 | 1/2004 | Soltanpour et al. | |
| 6,685,670 B2 | 2/2004 | Miles et al. | |
| 6,749,591 B1 | 6/2004 | McNally et al. | |

(56) References Cited

U.S. PATENT DOCUMENTS

| | | | |
|---|---|---|---|
| 6,750,468 B2 | 6/2004 | Malmstrom et al. | |
| D501,924 S | 2/2005 | Cise et al. | |
| 6,852,094 B2 | 2/2005 | Beck et al. | |
| D503,799 S | 4/2005 | Beck | |
| D503,978 S | 4/2005 | Beck | |
| D504,506 S | 4/2005 | Beck et al. | |
| D505,199 S | 5/2005 | Beck et al. | |
| 6,902,541 B2 | 6/2005 | McNally et al. | |
| 6,907,788 B2 | 6/2005 | Malmstrom et al. | |
| D507,647 S | 7/2005 | Beck et al. | |
| 6,923,785 B2 | 8/2005 | Miles et al. | |
| 6,942,636 B2 | 9/2005 | Holst et al. | |
| 6,949,376 B2 | 9/2005 | Kluttz et al. | |
| 6,979,311 B2 | 12/2005 | Miles et al. | |
| 7,037,302 B2 | 5/2006 | Vaillancourt | |
| D523,553 S | 6/2006 | Beck et al. | |
| 7,070,575 B2 * | 7/2006 | Beck et al. | 604/67 |
| 7,121,143 B2 | 10/2006 | Malmstrom et al. | |
| 7,150,727 B2 * | 12/2006 | Cise et al. | 604/246 |
| D536,783 S | 2/2007 | Cise et al. | |
| 7,207,780 B2 | 4/2007 | Bach | |
| 7,367,963 B2 * | 5/2008 | Cise et al. | 604/246 |
| 7,530,968 B2 | 5/2009 | Gonnelli | |
| 7,815,612 B2 * | 10/2010 | Cise et al. | 604/246 |
| 7,967,773 B2 * | 6/2011 | Amborn et al. | 604/19 |
| 7,976,513 B2 * | 7/2011 | Cise et al. | 604/246 |
| 8,343,111 B2 * | 1/2013 | Beck et al. | 604/250 |
| 8,425,470 B2 * | 4/2013 | Beck et al. | 604/250 |
| 2002/0117850 A1 * | 8/2002 | Wood et al. | 285/124.1 |
| 2002/0169424 A1 | 11/2002 | Miles et al. | |
| 2004/0220542 A1 | 11/2004 | Cise et al. | |
| 2004/0260332 A1 | 12/2004 | Dubrul et al. | |
| 2005/0004540 A1 | 1/2005 | McNally | |
| 2005/0096593 A1 | 5/2005 | Pope et al. | |
| 2005/0119625 A1 | 6/2005 | Miles et al. | |
| 2005/0209563 A1 | 9/2005 | Hopping et al. | |
| 2005/0277912 A1 | 12/2005 | John | |
| 2006/0058740 A1 | 3/2006 | Cise | |
| 2006/0142692 A1 | 6/2006 | Jacobson et al. | |
| 2007/0118078 A1 | 5/2007 | McNally | |
| 2007/0151346 A1 | 7/2007 | Malmstrom et al. | |
| 2008/0065008 A1 | 3/2008 | Barbut et al. | |
| 2008/0098798 A1 | 5/2008 | Riley | |
| 2008/0103445 A1 | 5/2008 | Blaine et al. | |
| 2008/0119782 A1 | 5/2008 | Steinman | |
| 2008/0134750 A1 | 6/2008 | Riley | |
| 2008/0208117 A1 | 8/2008 | Steinman | |
| 2008/0276911 A1 | 11/2008 | Woody | |
| 2009/0049919 A1 | 2/2009 | Hills | |
| 2009/0149801 A1 | 6/2009 | Crandall | |
| 2009/0254034 A1 * | 10/2009 | Beck et al. | 604/118 |
| 2010/0234809 A1 | 9/2010 | Kenley et al. | |
| 2012/0143140 A1 * | 6/2012 | Bierman et al. | 604/174 |

FOREIGN PATENT DOCUMENTS

| | | |
|---|---|---|
| EP | 0 150 666 | 9/1984 |
| EP | 0 276 356 | 8/1988 |
| EP | 0 423 978 | 10/1990 |
| EP | 0 483 794 | 10/1991 |
| GB | 2 338 759 | 12/1999 |
| JP | 05-042219 | 2/1993 |
| JP | 08105867 A | 4/1996 |
| JP | 10-048759 | 2/1998 |
| WO | WO 96/08666 | 3/1996 |
| WO | WO 96/17636 | 6/1996 |

OTHER PUBLICATIONS

The International Bureau of WIPO, International Preliminary Report on Patentability issued in International Application No. PCT/US2011/053955 Apr. 2, 2013.

* cited by examiner

ANTI FREE-FLOW OCCLUDER AND PRIMING ACTUATOR PAD

PRIORITY

The present application claims the benefit of U.S. Provisional Application Ser. No. 61/388,901, filed Oct. 1, 2010 which is herein incorporated by reference in its entirety.

THE FIELD OF THE INVENTION

The present invention relates to preventing undesired flow through tubing. More specifically, the present invention relates to preventing free flow and undesired flow in infusion tubing such as may be used for delivering nutritional feeding via a pump while selectively allowing flow through the infusion tube as desired.

BACKGROUND

Fluid delivery pumps are used for a variety of different purposes. Medical fluids are frequently delivered via a peristaltic pump. In medical applications, it is particularly important to control the fluid flow through the delivery tubing. Where medicine or nutritional fluids are delivered through the tubing, it is typically important to control the volume of fluid delivered as well as the rate of delivery. Unintended flow through the delivery tubing can result in inaccurate fluid delivery and can cause health problems for the patient in some cases.

In order to prevent unintended flow through medical delivery tubing, occluders are often used to selectively prevent flow through the tubing. The occluder is opened when it is desired to allow flow through the tubing. Available in-line occluders and the associated systems for allowing flow through the tubing and past the occluder suffer from several problems. One problem is the difficulty for a person to manually prime the delivery tubing in order to remove air from the tubing and fill the tubing with the liquid before using the delivery tubing in a pump to deliver fluid to a person. In-line occluders in particular have been difficult for persons to actuate to manually prime delivery tubing. While the person may load the delivery tubing into the pump and use the pump to advance the fluid, the pump delivers fluid at a slow rate and it can take quite a long time to do so. In emergencies, such a time delay may not be desirable. Additionally, the attending person may begin to perform other tasks while priming the pump and neglect to adequately monitor the pump while priming.

Another problem with occluders is that the actuators or systems used to open a flow passage past the occluder have proven somewhat inconsistent in their performance, and may not open a sufficiently large flow passage to not restrict flow. Restrictions in flow may affect the accuracy of the delivered fluid or the ability to monitor the fluid flow. The performance of available in-line occluders is limited both by the strength and design of the occluder as well as by the design of the actuator element used to create a flow path past the occluder.

Another problem is the reliability of the pump structures used to open a flow channel past the occluder once the occluder is properly loaded into a delivery pump. Prior art structures have been used to create a flow channel past the occluder, but these structures have often worked inconsistently or opened a flow passage which is insufficiently large for proper flow.

There is a need for an improved in-line occluder and actuator system for selectively allowing flow past the occluder.

There is a need for an occluder and actuator system which opens a larger flow path past the occluder and which reliably opens and closes the flow path. There is a need for an occluder and actuator system which reliably integrates with a pump, allowing the pump door to open a flow past the occluder when the door is closed. There is a need for an occluder and actuator system which allows a person to manually open a flow passage past the occluder easily and consistently.

SUMMARY OF THE INVENTION

It is an object of the present invention to provide an improved in-line occluder and actuator system for selectively allowing flow past the occluder.

According to one aspect of the invention, a fluid delivery cassette is provided which has an occluder and infusion tubing, and which has an actuator formed as a part of the cassette. The actuator allows a person to manually allow flow past the occluder quickly and reliably. The person may thus manually prime the tubing before loading the tubing into a pump or allow fluid to flow through the tubing by gravity.

According to one aspect of the invention, an occluder and actuator are provided which allow for a large flow channel to be opened past the occluder. An actuator design is provided which pushes and stretches the pump tubing to one side of the occluder and opens a single large flow passage past the occluder. An occluder is provided which has been significantly strengthened to resist bending and breaking when a large force is applied to the occluder by the actuator.

According to another aspect of the invention, a delivery cassette and pump are provided where the pump door interacts with the actuator assembly of the cassette to open flow past the occluder when the cassette is properly loaded and when the door is closed.

These and other aspects of the present invention are realized in an in-line occluder and actuator system as shown and described in the following figures and related description.

BRIEF DESCRIPTION OF THE DRAWINGS

Various embodiments of the present invention are shown and described in reference to the numbered drawings wherein.

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single figure, and as such, multiple figures are presented to separately illustrate the various details of the invention in greater clarity. Similarly, not every embodiment need accomplish all advantages of the present invention.

DETAILED DESCRIPTION

The invention and accompanying drawings will now be discussed in reference to the numerals provided therein so as to enable one skilled in the art to practice the present invention. The drawings and descriptions are exemplary of various aspects of the invention and are not intended to narrow the scope of the appended claims.

Figure 1A:
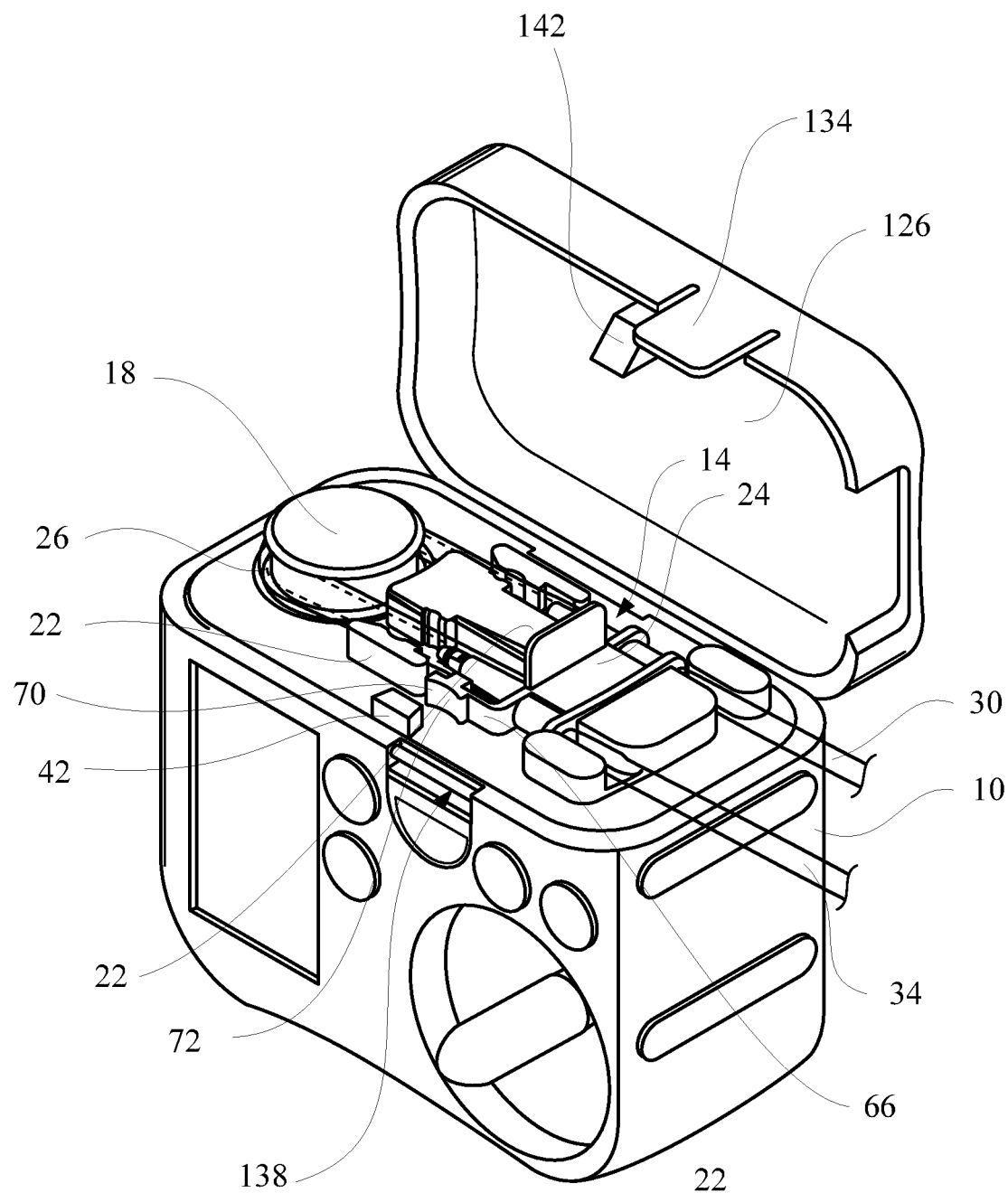
FIGS. 1A and 1B show perspective views of a pump and infusion cassette of the present invention.

Turning now to FIG. 1A, a perspective view of a pump 10 and infusion cassette 14 of the present invention is shown. The pump 10 is a peristaltic pump typically used for medical applications such as drug delivery, IV applications, or feeding. The pump 10 includes a pumping rotor 18, various structures 22 to locate and secure the infusion cassette 14, and auxiliary devices such as pressure sensors and air bubble detectors as are necessary for the application. The infusion cassette 14 includes a cassette body 24 and pumping tubing 26 which is wrapped around the pump rotor 18. The cassette body 24 is attached to inflow tubing 30 which is connected to a fluid supply, and outflow tubing 34 which is connected to a patient. The pump tubing 26 is typically flexible silicone tubing. The inflow tubing 30 and outflow tubing 34 are typically vinyl tubing.

The cassette body is formed with an in-line occluder to prevent uncontrolled flow through the pump tubing 26. To improve the ease of use of the cassette 14, the cassette body has a priming arm 66 which is disposed adjacent the occluder. The priming arm includes an actuator pad 70 which interacts to allow flow past the occluder 62. The side of the actuator pad 70 which faces towards the occluder 62 has an engagement surface for engaging the tubing 26 and allowing flow past the occluder. The side of the actuator pad 70 which faces away from the occluder 62 includes a rounded finger depression 72 which receives the finger or thumb of a user to allow the user to manually open a flow passage past the occluder 62. The priming arm may be used to manually prime the cassette 14 before loading the cassette into the pump 10, and also interacts with the pump 10 to allow flow past the occluder once the cassette 14 is properly loaded in the pump.

The pump 10 includes a door 126 which is attached to the pump 10 via a hinge. The door includes a latch 134 which interacts with the pump to hold the door closed, and also includes a projection 142 which interacts with the priming arm 66 to open a flow passage past the occluder 62. The pump 10 includes a door support post 42 which interacts with the pump door projection 142 to allow flow past an occluder 62 which is part of the cassette body 24 after the pump door is closed. The door support post 42 is disposed adjacent the actuator pad 70 with a space therebetween. The projection 142 fits between the support post 42 and the actuator pad 70 and, when placed therebetween, forces the actuator pad 70 towards the occluder 62 to engage the tubing 26 and open a flow passage past the occluder.

Figure 1B:
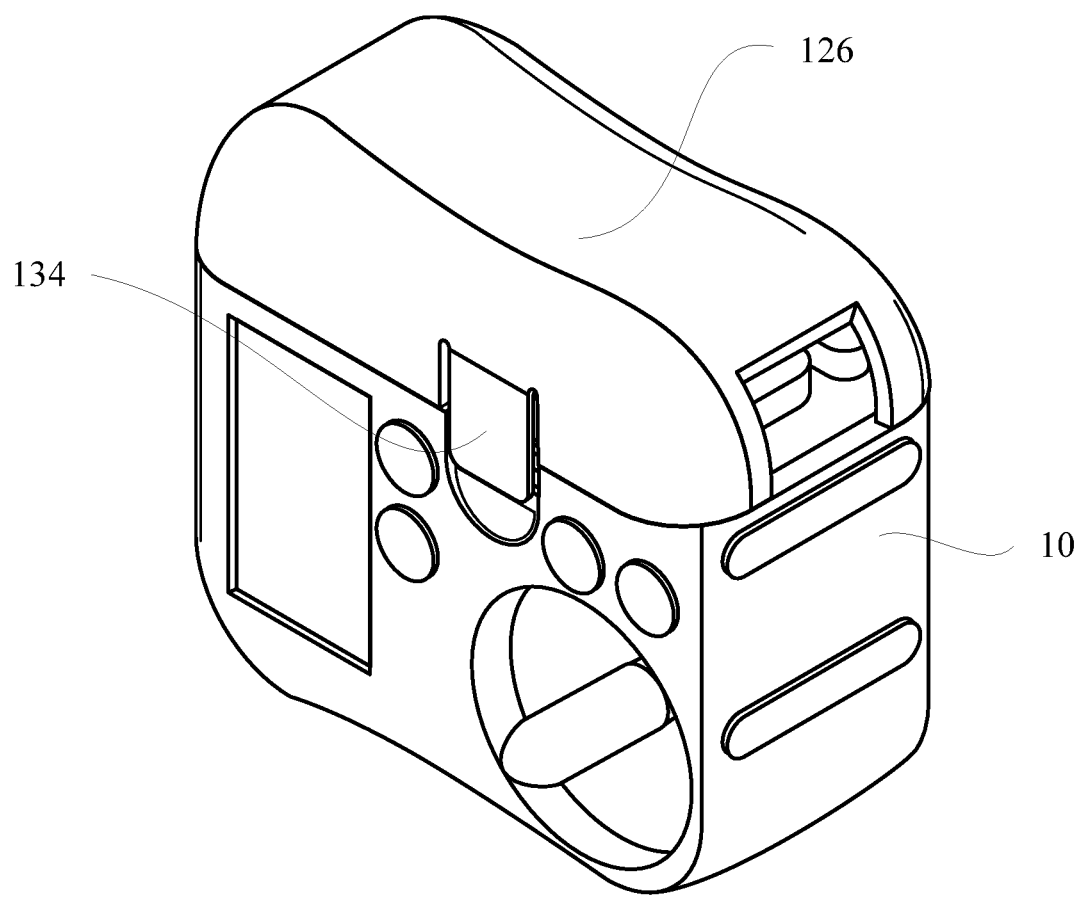

FIG. 1B shows the pump 10 with the door 126 in a closed position. In this position, the projection 142 has engaged the door support post 42 and the actuator pad 70 to press the actuator pad against the tubing 26 and create a flow passage between the occluder 62 and the tubing 26.

Figure 2A:
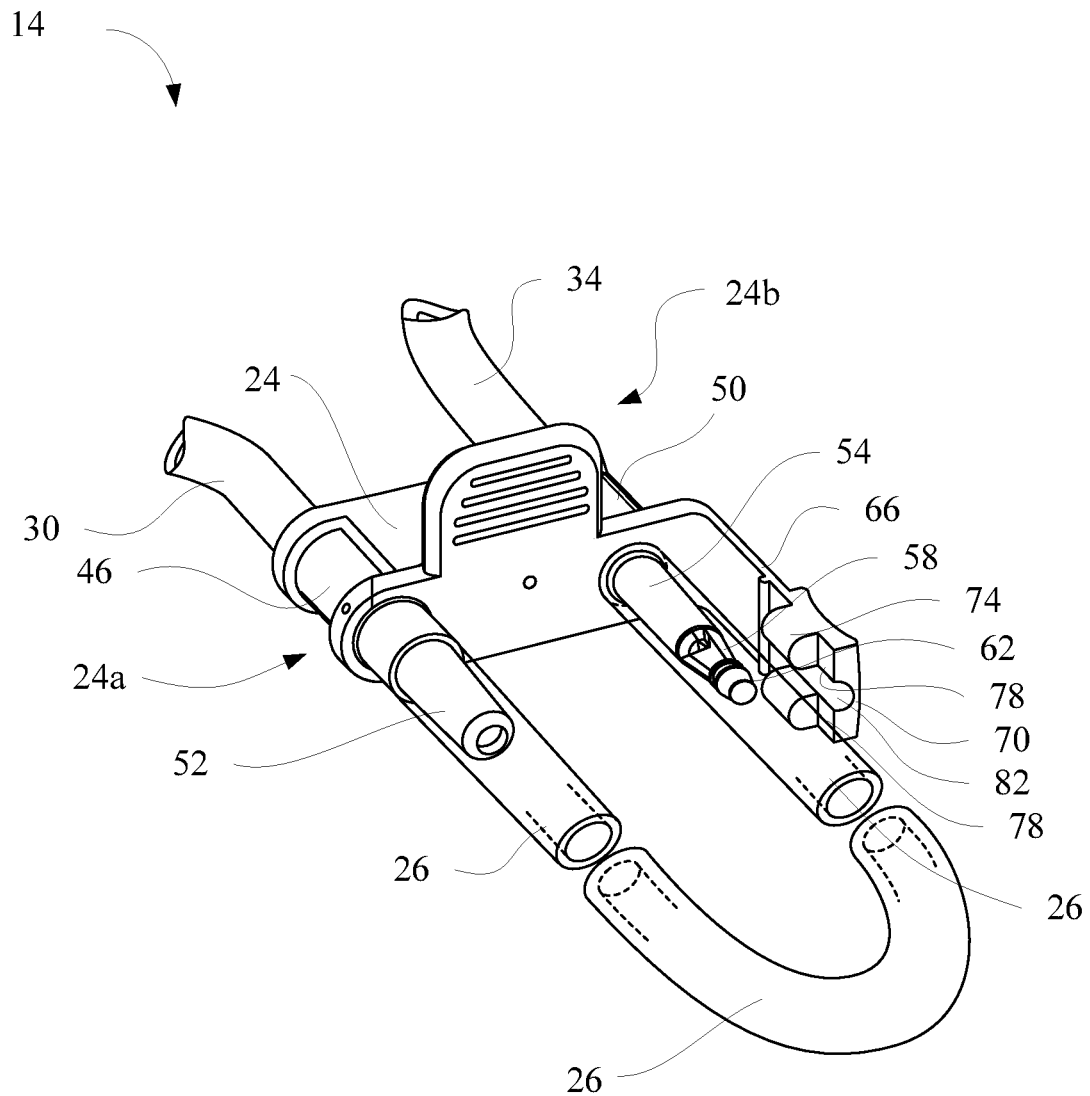
FIGS. 2A through 2D show perspective and top views of the infusion cassette.
Figure 2B:
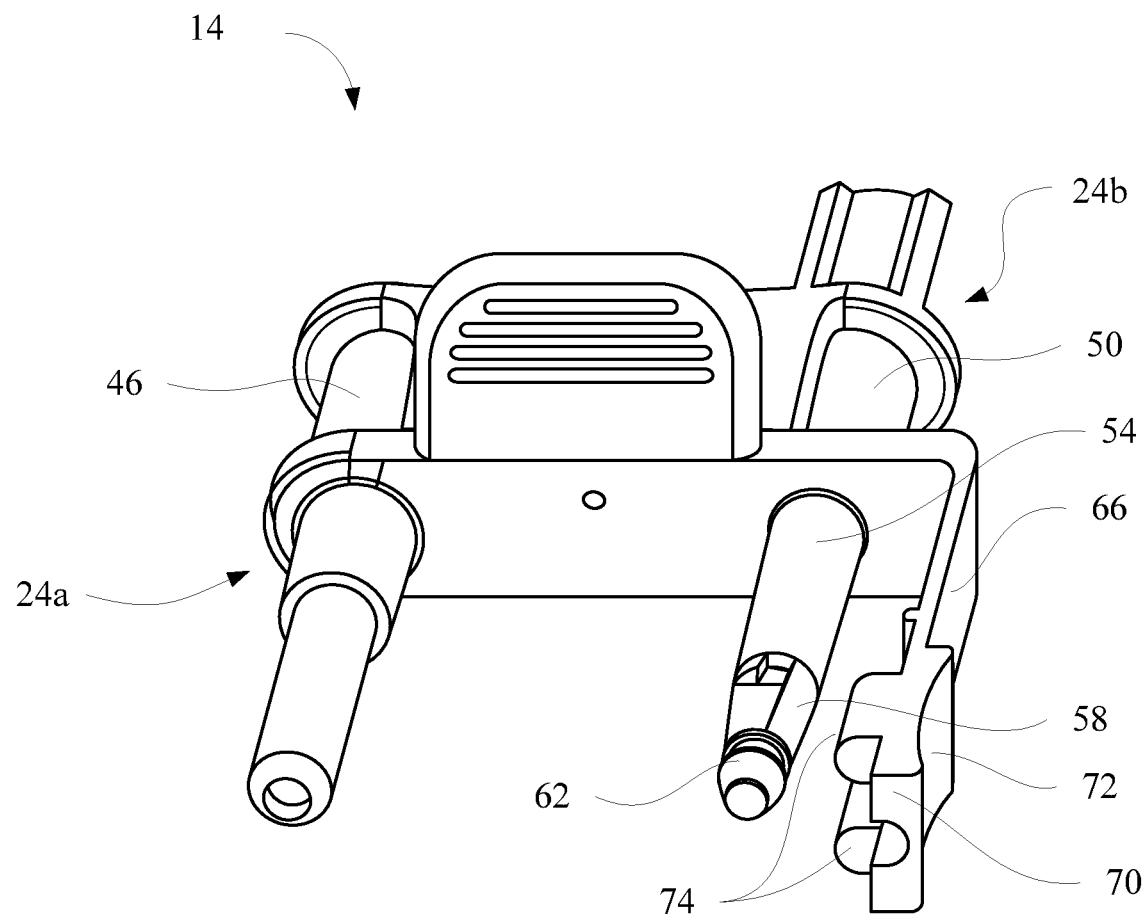
Figure 2C:
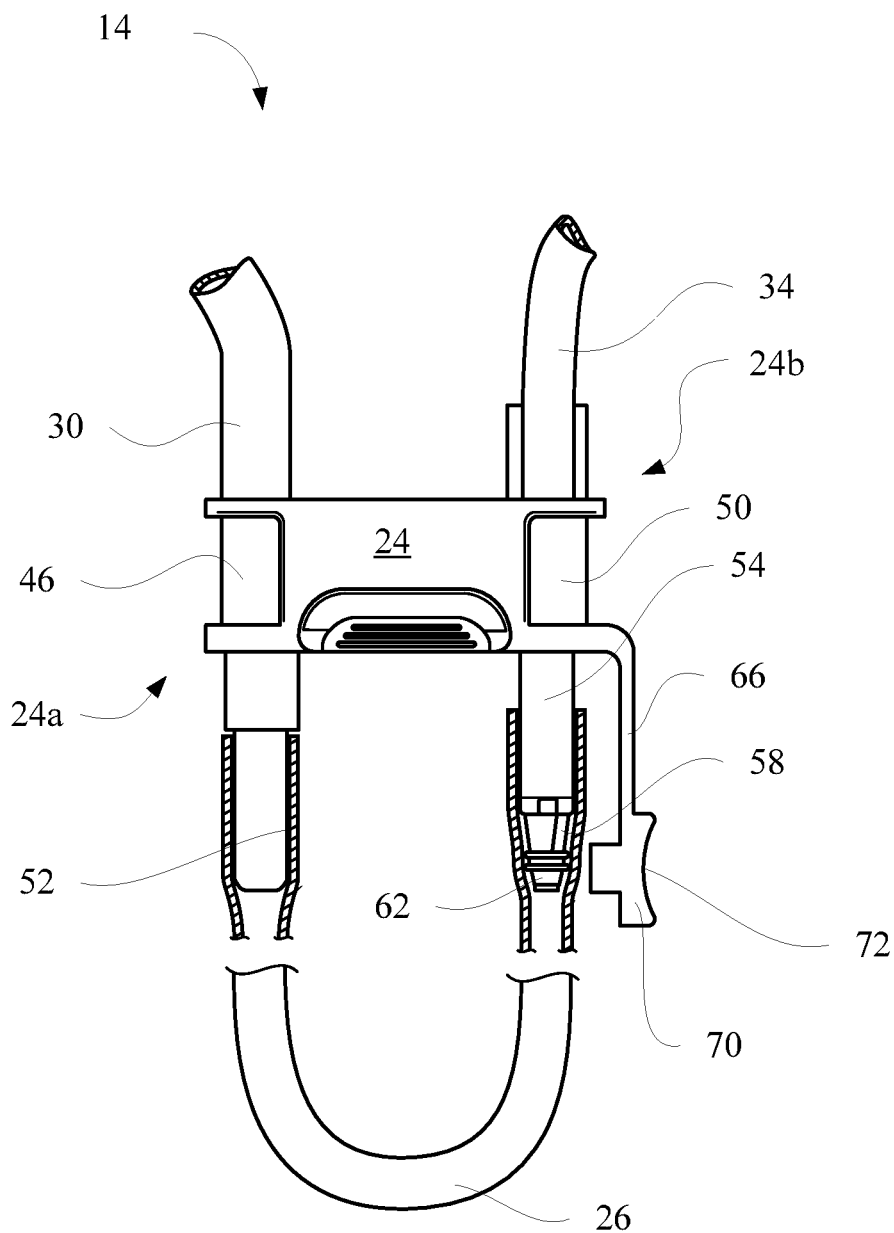
Figure 2D:
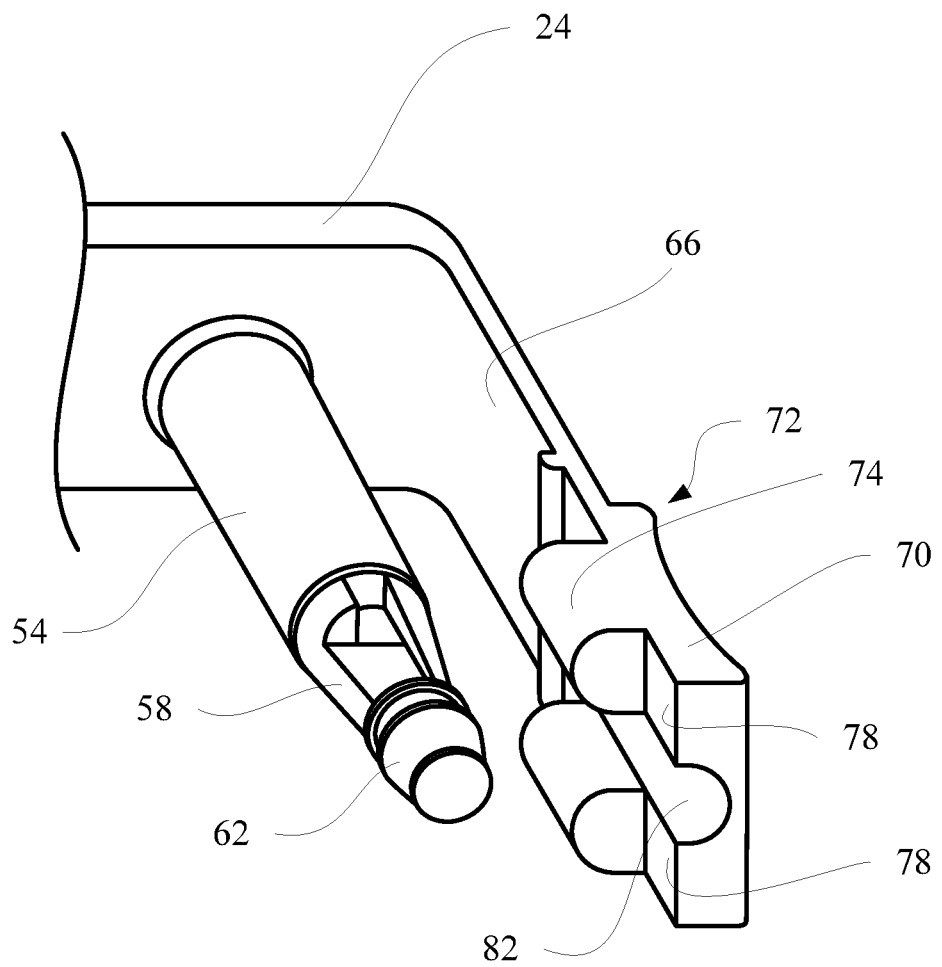

FIGS. 2A and 2B show perspective views of the cassette 14. FIG. 2C shows a top view of the cassette 14. FIG. 2D shows a partial perspective view of the cassette occluder and priming arm. The cassette 14 is a unitary, one-piece structure having the various parts such as the cassette body, occluder, connectors and actuator arm as discussed herein. The cassette body 24 connects the inflow tubing 30, outflow tubing 34 and pump tubing 26. As seen, a first side 24a of the cassette body 24 forms a first connector 46 which receives the inflow tubing 30 and a first end of the pump tubing 26. A second side 24b of the cassette body 24 forms a second connector 50 which receives the outflow tubing 34 and a second end of the pump tubing 26. The body 24 connects the first connector 46 and second connector 50 together, the first and second connectors being disposed generally parallel to each other and separated laterally by the body. The pump tubing 26 is held in a loop and is placed around the pump rotor. The first connector 46 has a cylindrical or barbed body 52 which holds the pump tubing 26. The second connector 50 has a cylindrical body 54, a stem 58 attached to the body, and an occluder 62 which is attached to the stem so that the stem spaces the occluder apart from the body. The body 54, stem 58 and occluder 62 are placed in the bore of the pump tubing 26. The first connector body 52 and second connector body 54 are larger than the tubing bore and grip the tubing. The occluder 62 is slightly larger in diameter than the pump tubing bore so that the occluder seals against the bore and, in this state, prevents flow through the pump tubing.

A priming arm 66 is disposed adjacent the body 54 and occluder 62. As shown, the priming arm 66 extends generally parallel to the body 54 and occluder 62. The priming arm 66 has an actuator pad 70 formed on the end of the arm 66. The actuator pad 70 is adjacent the occluder 62 so that when the priming arm 66 is bent inwardly towards the occluder 62 the actuator pad contacts the pump tubing 26 which is laterally adjacent to the occluder. The side of the actuator pad 70 which faces the occluder 62 is formed with two rounded projections 74 disposed longitudinally adjacent the occluder 62, a tip portion 78 disposed slightly upstream from the occluder 62, and a channel 82 extending longitudinally along the actuator pad 70 and between the projections 74. As the actuator pad 70 is pressed against the pump tubing 26, a flow channel is opened between the occluder 62 and the pump tubing. The side of the actuator pad 70 which is opposite the occluder 62 has a rounded depression 72 for receiving the finger or thumb of a user. This makes the actuator more intuitive for manual priming of the infusion cassette 14 and reduces the likelihood that the user's finger or thumb slips while manually allowing flow past the occluder. FIGS. 2B and 2C better illustrate the finger depression 72 as well as other aspects of the cassette 14.

Figure 3:
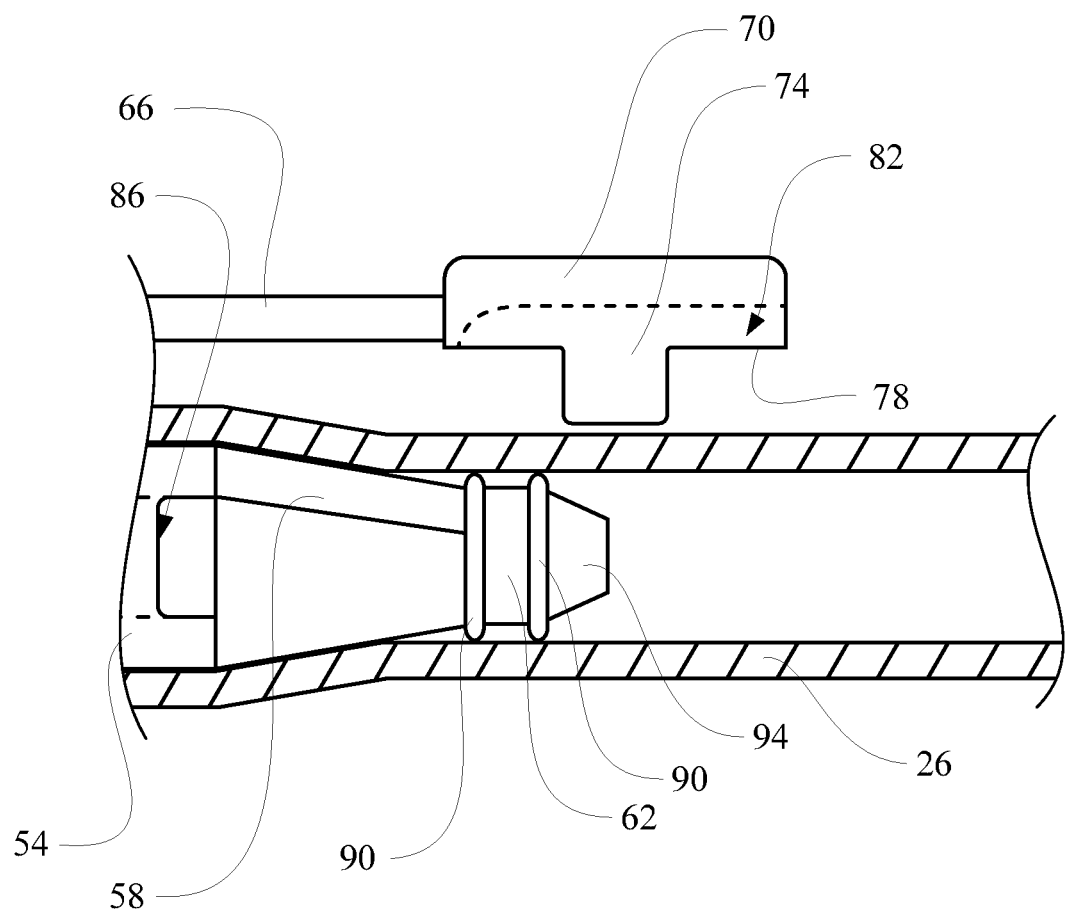
FIGS. 3 through 5 show partial cross-sectional side views of the occluder and actuator pad of the infusion cassette.
Figure 4:
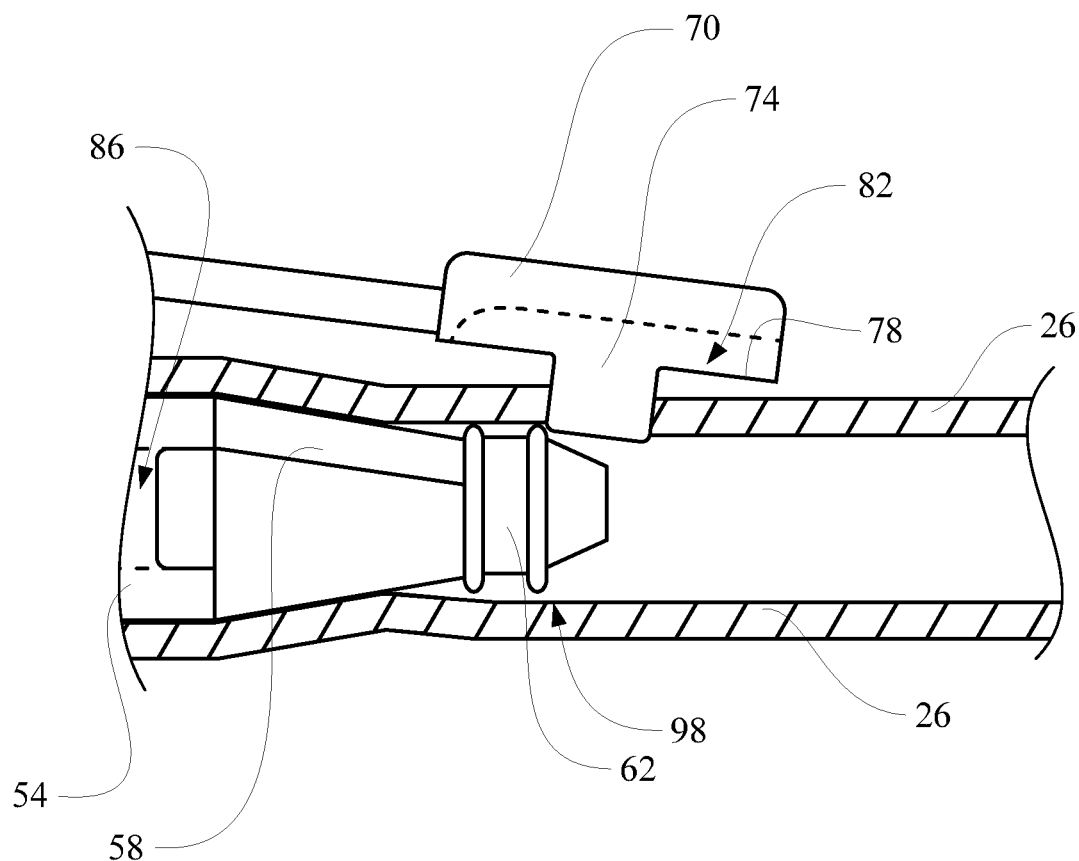
Figure 5:
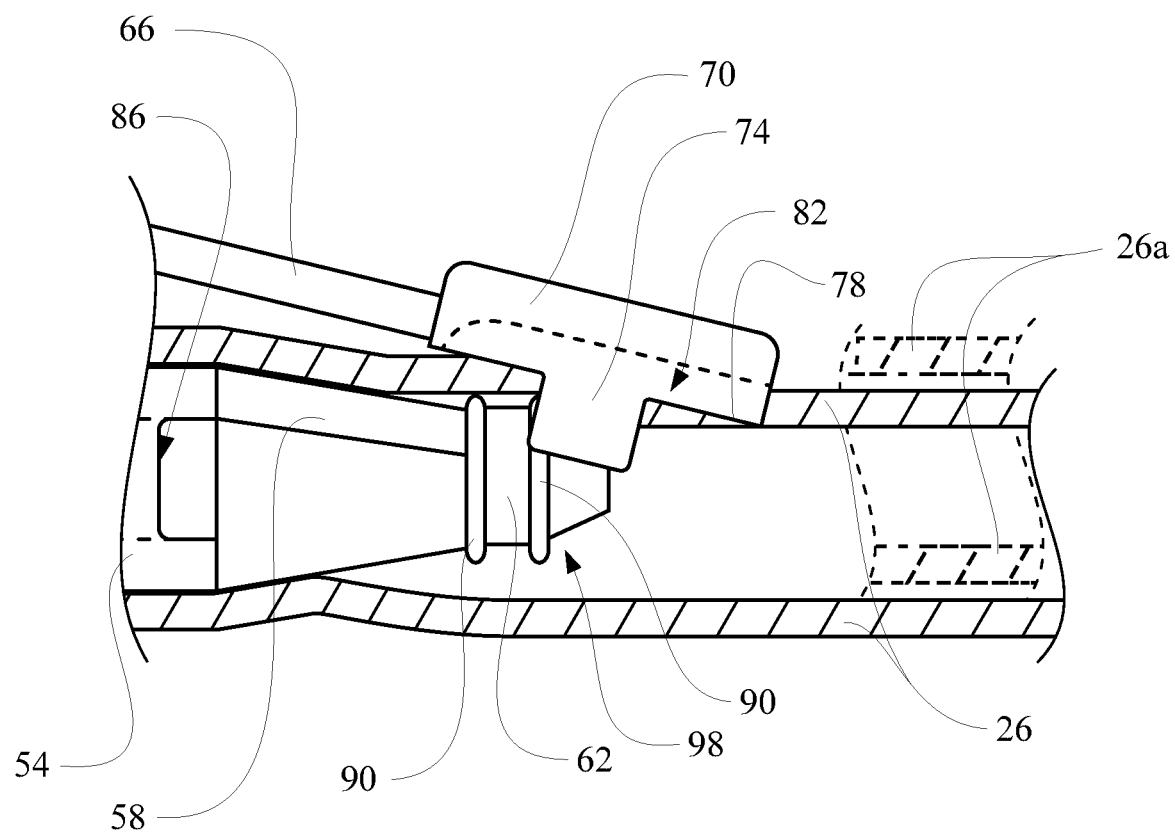

FIGS. 3 through 5 show side views of the occluder 62 and priming arm 66 moved through various stages of actuation in order to allow flow past the occluder. The connector body 54 is inserted into the pump tubing 26. As shown, the connector body 54 has a bore 86 therethrough. The stem 58 is formed with a 'T' shaped cross section. The stem 58 has a side wall disposed perpendicular to the movement of the priming arm 66 and a web disposed parallel to the movement of the priming arm. The side wall and web extend longitudinally from the body 54 and connect the body 54 and occluder 62 to each other. The occluder 62 has a cylindrical shape with two ribs 90 formed thereon and a tapering front portion. The ribs 90 engage the bore of the pump tubing 26 to form a seal and prevent flow through the pump tubing. The end 94 of the occluder 62 tapers to a smaller diameter, allowing the pump tubing 26 to bend sideways to better open a flow channel through the tubing. When a flow path is opened, fluid flows between the occluder 62 and the tubing wall, around the stem 58, and through the bore 86 in the connector body 54.

It can be seen how, according to a preferred embodiment, the projections 74 on the actuator pad 70 are slightly upstream of the occluder ribs 90; the downstream edge of the projections 74 being aligned with the upstream rib 90. In other words, the proximal (relative to the connection of the priming arm 66 to the cassette body 24) side of the projections 74 is aligned with the distal rib 90. This arrangement between the projections 74 and occluder 62 places the projections 74 over both of the ribs 90 when the priming arm 66 bends inwardly to open a flow channel past the occluder. The tip portion 78 of the actuator pad 70 is upstream of the projections 74. The tip portion 78 of the actuator pad 70 does not extend towards the tubing 26 as far as the projections 74. The channel 82 extends longitudinally along the actuator pad 70, extending between the projections 74 and along the tip portion 78. The channel aids in bending and positioning the tubing 26 when the priming arm 66 is pressed against the tubing.

FIG. 4 shows the actuator pad 70 pressed against the pump tubing 26. The actuator pad 70 is moved partially between the first non-engaging rest position shown in FIG. 3 and the second fully engaging actuated position shown in FIG. 5. The projections 74 engage the pump tubing 26 as the actuator pad 70 is moved inwardly as shown. This causes the portion of the pump tubing 26 between the projections 74 to become stretched and pushes the pump tubing away from the actuator pad 70, causing a flow passage 98 to open between the occluder 62 and the pump tubing 26. Once a flow passage 98 has been opened, fluid may flow between the pump tubing 26 and the occluder 62, past the stem 58, and through the bore 86 in the body 54.

FIG. 5 shows the actuator pad 70 moved into the second actuated position. It can be seen how the projections 74 are now positioned over the ribs 90. The projections 74 have further stretched the portion of the pump tubing 26 between the projections, and have formed a larger flow passage 98 between the pump tubing 26 and the occluder 62. When the actuation pad 70 is in the second position as shown, the tip 78 of the actuation pad 70 contacts the pump tubing 26 and presses a portion of the pump tubing which is upstream from the occluder laterally, displacing the pump tubing in the direction of movement of the priming arm 66. This displacement of the pump tubing 26 is shown in comparison to the dashed pump tubing portion 26a which indicates the original undisplaced position of the pump tubing 26.

The actuator pad 70 thus engages the pump tubing 26 in two different manners in order to more effectively create a flow passage 98. The projections 74 stretch the pump tubing 26 around the occluder 62 and push the pump tubing away from the actuation pad and the tip of the actuation pad also presses on the pump tubing upstream from the occluder to further move the pump tubing away from the actuation pad 70. The combined stretching and displacement of the pump tubing 26 creates a large flow passage 98 between the pump tubing and the occluder 62. The actuator pad 70 thus provides a significant improvement over previous methods of creating a flow passage past the occluder 62 by opening a significantly larger flow passage 98 and by more reliably creating the flow passage. It can also be seen how, when the priming arm 66 is fully pressed against the tubing 26, the projections 74 are disposed adjacent both of the ribs 90.

Figure 6:
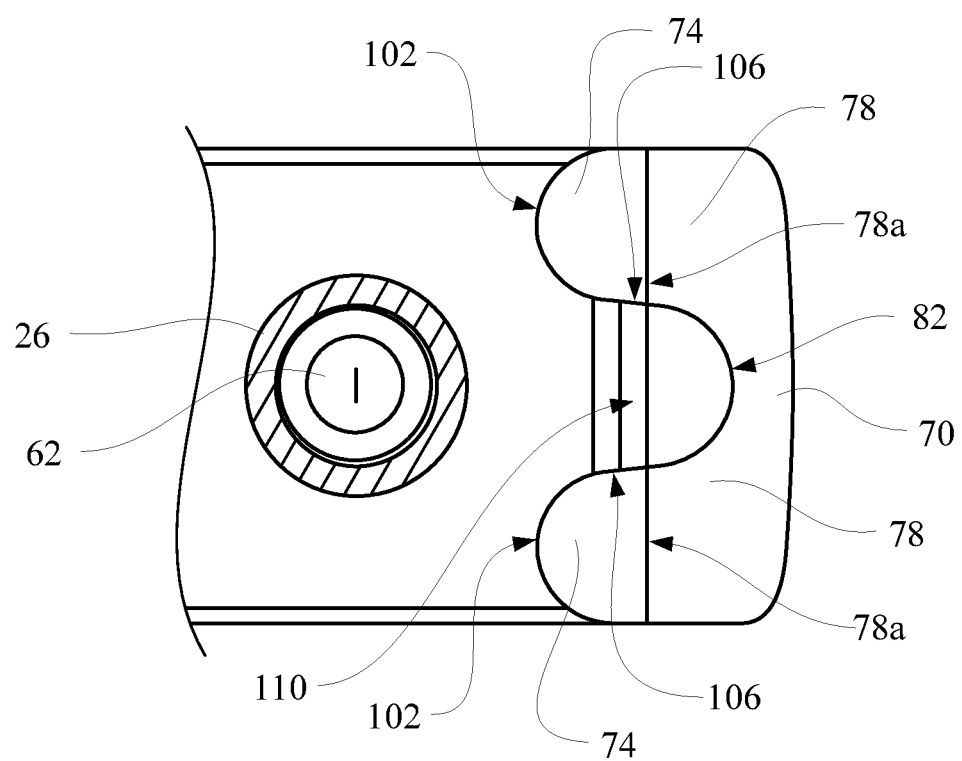
FIGS. 6 through 8B show partial cross-sectional end views of the occluder and actuator pad.

FIG. 6 shows an end view of the occluder 62 and actuator pad 70 in the first, non-actuating position (as shown in FIG. 3). The shape of the actuator pad 70 can more readily be seen. As has been discussed, the cassette 14 is often used for medical applications such as delivering feeding solutions. As such, the occluder 62 is often about one eighth of an inch in diameter. The bore of the pump tubing 26 is slightly smaller than the diameter of the occluder 62 so that the occluder seals against the pump tubing. The functional portion of the actuator pad 70, as discussed, is largely defined by the projections 74, the channel 82 and the tip portion 78. The actuator pad functional surfaces include the radiused ends 102 of the projections 74, the radiused channel 82, and relatively flat surfaces 106 connecting the radiused ends 102 and the channel 82.

According to a preferred embodiment, the radiused ends 102 of projections 74 have a radius of curvature which is approximately equal to the radius of the occluder 62 and occluder ribs 90 (as the occluder ribs are relatively small). It is currently preferred that the channel 82 have a radius of curvature which is also approximately equal to the radius of the occluder 62. The flat surfaces 106 connecting the radiused ends 102 and the surface of the channel 82 are disposed at a slight angle to each other such that they form a slot between the projections which tapers and is narrower at the bottom than at the top. The flat surfaces may be disposed at an angle of about 5 to 25 degrees relative to each other. It is currently preferred that the flat surfaces 106 are disposed at an angle which is between about 15 and 20 degrees relative to each other; with an angle of about 18 degrees being currently preferred. For ease of molding the actuator pad 70, it is currently preferred that the radiused ends 102, flat surfaces 106 and channel 82 are flat longitudinally along the axis of the occluder 62. The surfaces 78a of the tip portion 78 which face towards the occluder 62 are typically flat for ease of manufacture.

The shape of the actuator pad 70 allows for the formation of a large flow passage 98, and allows the occluder to reliably seal against the tubing 26 when the actuator pad 70 is not pressed against the tubing 26. The radiused ends 102 of the projections 74 allow the projections to push into the pump tubing 26 slightly and to grip the pump tubing well as the actuation pad 70 engages the pump tubing. As the actuation pad 70 moves further towards the occluder 62, the pump tubing 26 is engaged by the flat surfaces 106 which more tightly grip the pump tubing and allow for a higher degree of stretching to occur to the portion of the pump tubing which is between the projections 74. The angle formed between the flat surfaces 106 both allows these flat surfaces 106 to more tightly grip the pump tubing 26 as the pump tubing is pushed closer to the channel 82, and also allow the occluder 62 and pump tubing 26 to be easily released from between the projections 74 when the actuation pad 70 is no longer pushed towards the occluder 62, making the occluder more reliable.

The contact surfaces of the actuation pad 70 which engage the tubing adjacent the occluder 62 form an actuation channel 110 which engages the pump tubing 26. The actuation channel 110 is formed by the radiused ends 102, flat surfaces 106 and curved channel 82. The actuation channel curves outwardly at the top (in the area of radiused ends 102) to better grip the tubing 26 as the occluder 62 is forced into the actuation channel 110. The actuation channel 110 is also tapered so that it gets progressively narrower as the occluder 62 is pressed deeper into the channel, increasing the grip on the pump tubing 26 and better stretching and moving the pump tubing to form a flow passage 98. The bottom of the actuation channel 110 is formed by curved channel 82. The bottom of the actuation channel 110 limits how deep the occluder 62 can slide into the channel, eliminating the possibility that the occluder and pump tubing 26 can become stuck in the actuation channel 110 and ensuring that the occluder and pump tubing easily exit the channel when the actuation pad 70 is not pressed against the occluder 62.

Figure 7:
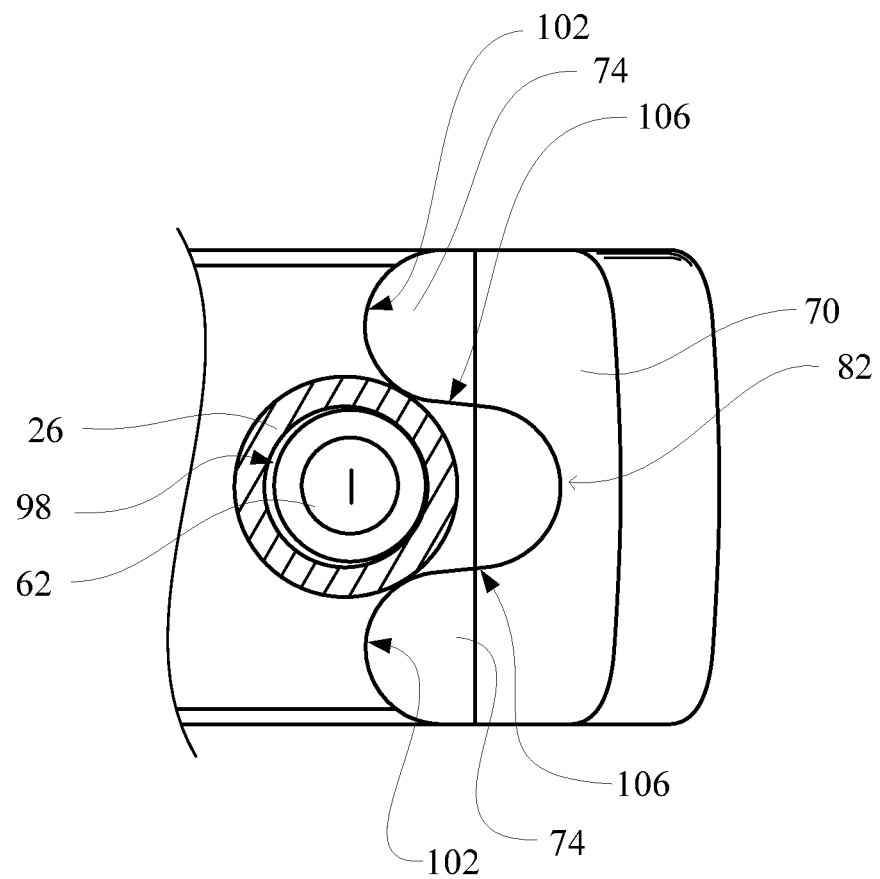

FIG. 7 shows an end view of the actuation pad 70 and occluder 62 in the intermediate actuation position which is shown in FIG. 4. It can be seen how the projections 74 engage the pump tubing 26 and, by stretching and pushing the pump tubing, form a flow passage 98 between the pump tubing and occluder 62.

Figure 8:
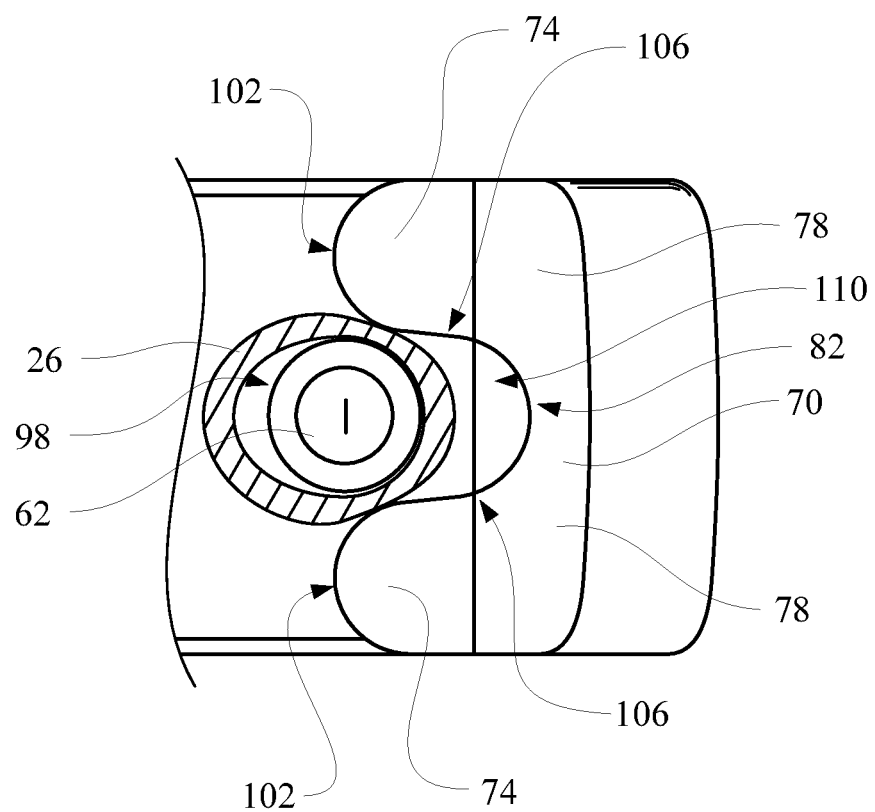

FIG. 8 shows another end view of the actuation pad 70 and occluder 62 in the second, actuating position shown in FIG. 5. It can be seen how the occluder 62 is moved between the projections 74. The radiused ends 102 of the projections and the tapering channel formed by the flat surfaces 106 has stretched the portion of the pump tubing 26 which is between the projections 74, pushing the pump tubing outwardly and making a large flow passage 98 between the pump tubing and the occluder 62. The actuation pad 70 can also be pressed further against the occluder 62 and tubing 26, contacting the tubing 26 against the bottom of the channel 82. Although not necessary, this can hold the tubing 26 securely while forming a flow channel 98. It is thus seen how the actuation channel 110 has a shape which has been found to maximize the reliability of the occluder and to open a large flow path past the occluder when desired.

Figure 8B:
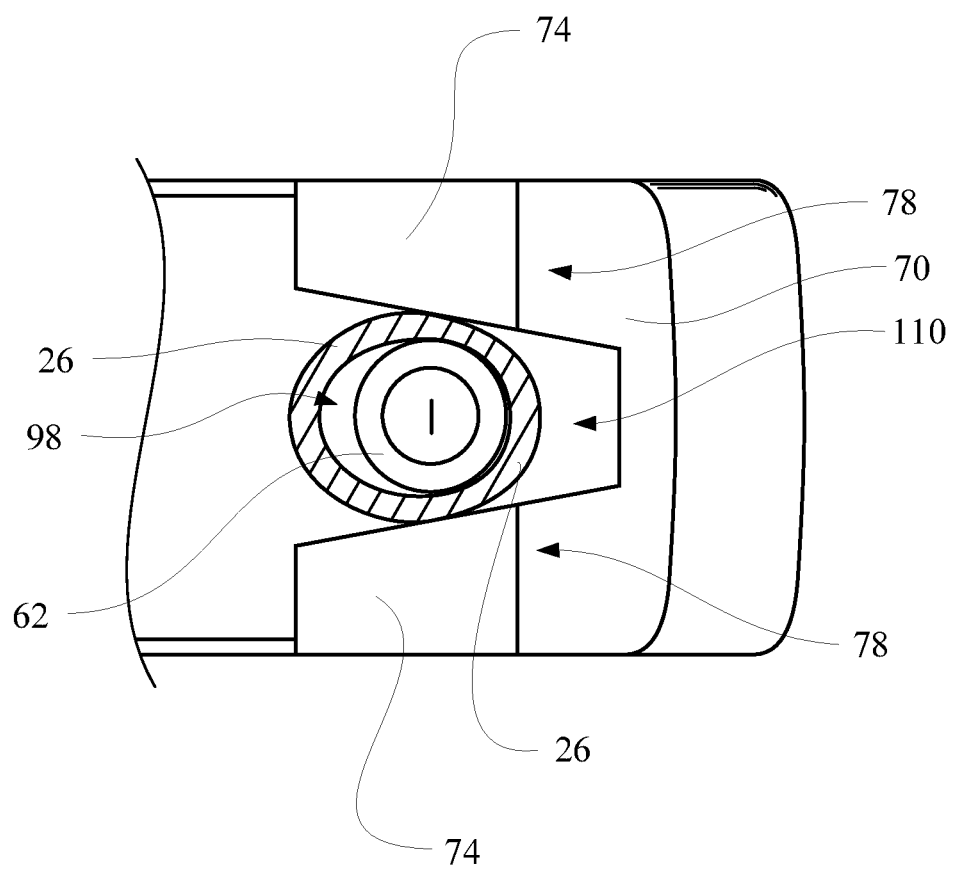

FIG. 8B shows another end view of an actuation pad 70 which functions similarly to that of the remaining figures. Unless discussed otherwise, the actuation pad 70 of FIG. 8B is used with the other structures and features of the pump and cassette as discussed with respect to the other figures. The actuation pad 70 varies in that the projections 74 are extended and do not have a rounded front end. Rather, the projections form a deeper actuation channel 110. The actuation channel tapers, being wider near the opening and narrower near the bottom of the actuation channel. The side surfaces 106 of the actuation channel 110 are disposed at an angle of approximately 18 degrees relative to each other. When the actuation pad 70 is forced towards the occluder 62, the pump tubing 26 is stretched and pushed to form a flow passage 98 as discussed.

The actuator pad 70 of FIGS. 6-8 (and the other figures of the application) has been found to be advantageous over a more simple actuation pad as shown in FIG. 8B, however. The actuation pad 70 of FIGS. 6-8, because of the curved ends 102 of the projections 74, does not require as much lateral movement as the actuation pad of FIG. 8B and releases and grips the projection better, increasing the reliability of the actuator pad 70 as used to prime the infusion cassette and allow flow past the occluder.

Figure 9:
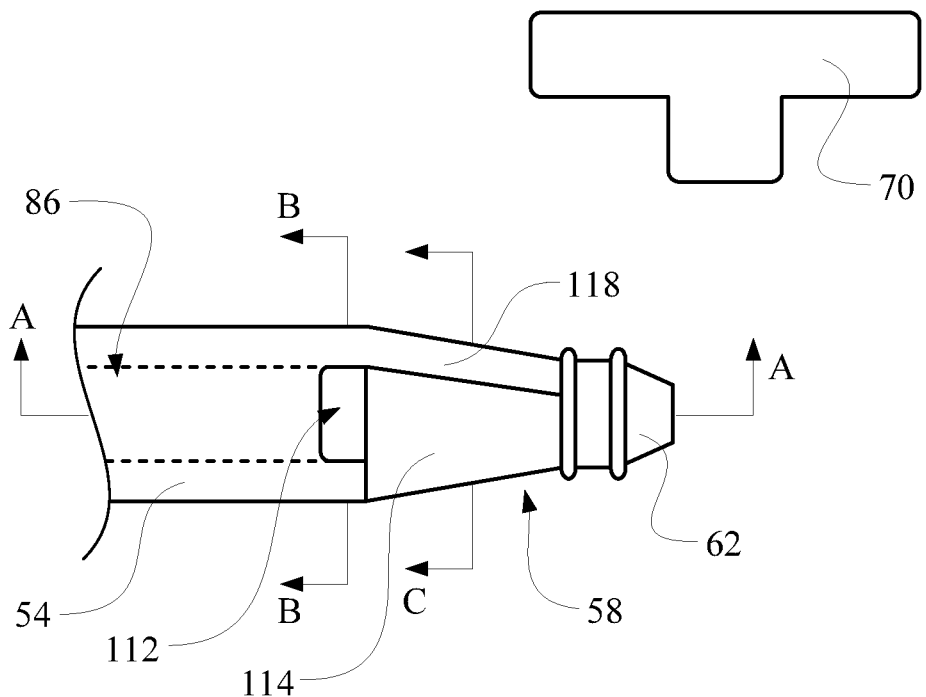
FIGS. 9 through 13 show additional views of the occluder and stem.
Figure 10:
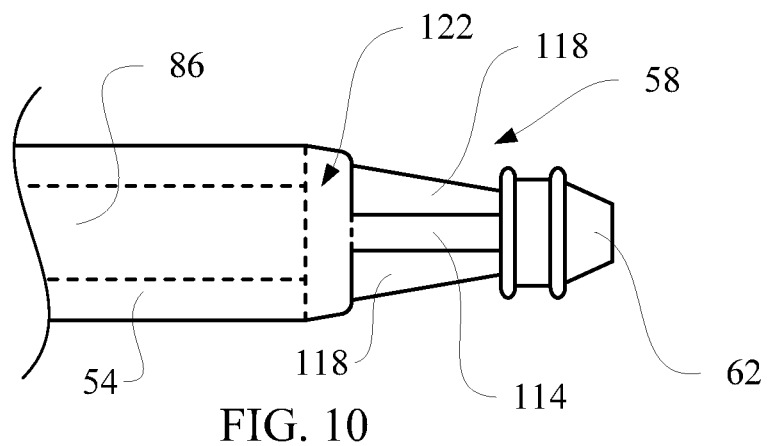
Figure 11:
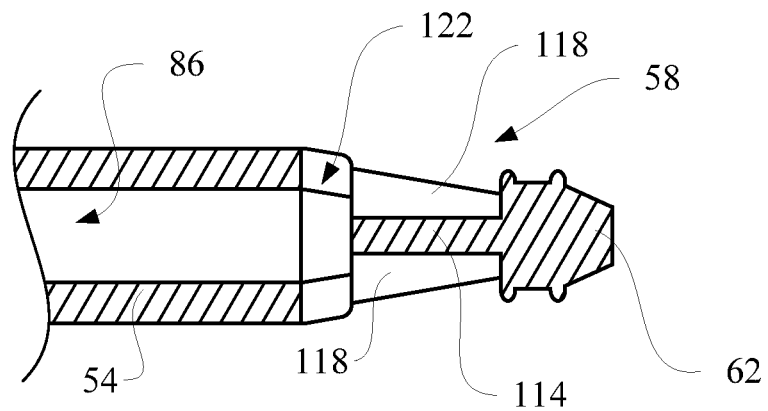
Figure 12:
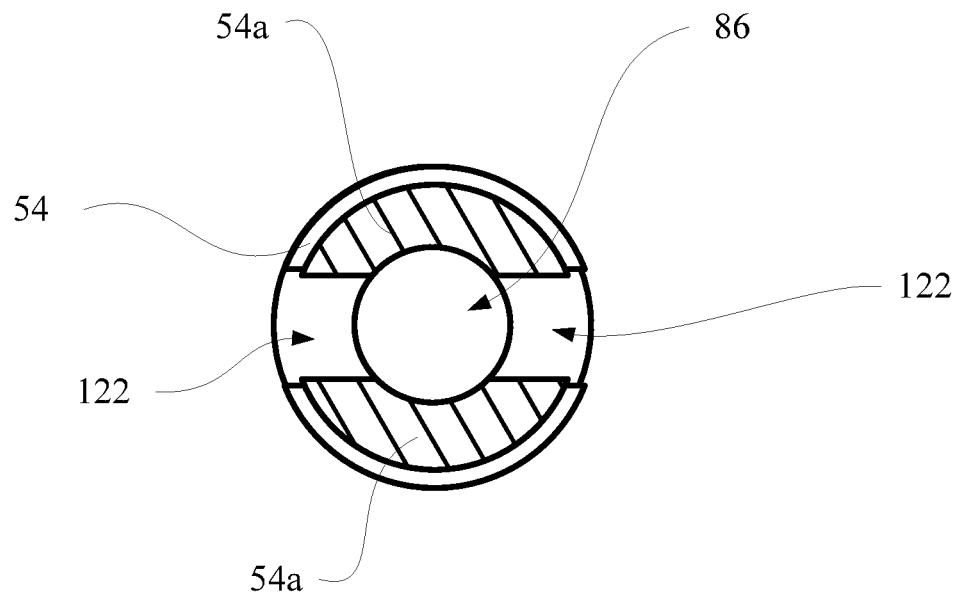
Figure 13:
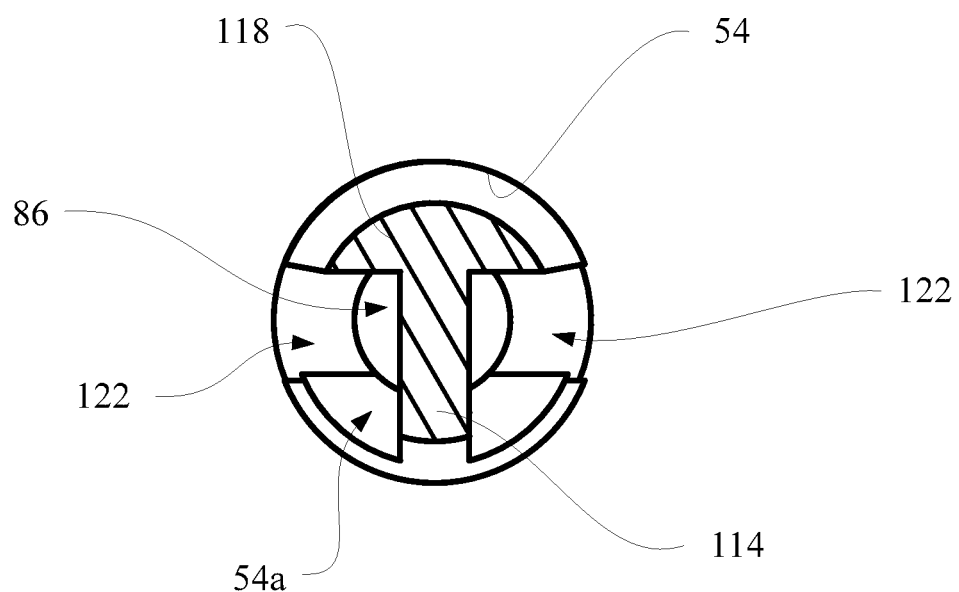

FIGS. 9 through 13 show detailed views of the occluder stem 58. FIG. 9 shows a view of the stem 58 with the actuation pad 70 included for reference. FIG. 10 shows a view from the side of the stem 58 opposite the actuation pad. FIGS. 11 through 13 show cross-sectional views taken along lines A-A, B-B and C-C of FIG. 9. The occluder body 54, stem 58 and occluder 62 are shown. The actuation pad 70 is shown for reference to indicate how force is applied to the occluder 62. In order to reliably create a large flow passage 98, the actuator pad 70 places a large lateral force on the occluder 62. Stem 58 provides increased unidirectional bending strength while still providing an adequate flow path around the stem 58. The stem 58 has a generally 'T' shaped cross section.

The stem 58 includes a center web 114 extending across the center and side of the stem sway from the actuator pad 70 and includes a side wall 118 disposed perpendicular to the center web on the side of the stem which is adjacent the actuator pad. The side wall 118 is disposed perpendicular to the direction of movement of the actuation pad 70 in engaging the occluder 62 and the web 114 is disposed parallel to the direction of movement of the actuation pad 70. Thus, when the actuator pad 70 presses against the occluder 62, the side wall 118 is placed in tension and the center web 114 is largely placed in compression. An opening 122 is formed adjacent the base of the stem 58. The opening 122 extends parallel to the side wall 118. The opening 122 connects the bore 86 of the cylindrical body 54 to the space adjacent the center web 114. When a flow passage 98 is opened between the occluder 62 and the pump tubing 26, fluid is able to flow past the occluder, around and adjacent to the center web 114, through opening 122 and into the bore 86. The 'T' shaped stem 58 and the design of the fluid pathway through the stem achieves a stem 58 which provides increased strength while still maintaining an adequate fluid flow path which does not overly restrict flow. The 'T' shaped stem 58 has shown an increased resistance to bending and breaking under the elevated lateral forces which are applied by the actuator pad 70.

FIG. 11 better shows the internal structure of the stem 58. It can be seen how the fluid is able to flow past the center web 114, through the opening 122, and into the bore 86. FIG. 12 shows how the opening 122 passes laterally through the end of the cylindrical body 54, leaving broad solid body portions 54a to support the stem 58. The stem 58 eliminates thin elongate sections of material which allow for bending, deflection and breakage. FIG. 13 shows how the center web 114 and side wall 118 are arranged in a 'T' shape. The side wall 118 has a rounded outer surface.

Figure 14:
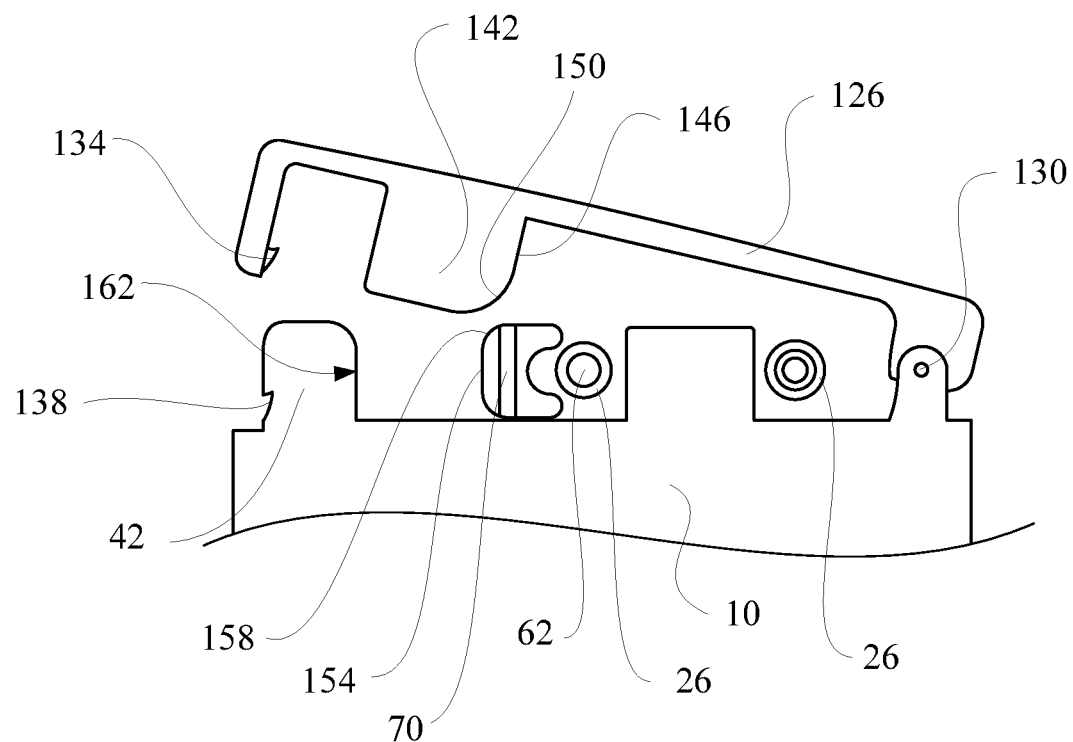
FIGS. 14 and 15 show partial views of the pump, cassette, and pump door.

FIG. 14 shows a partial cross-sectional view of the pump 10, actuation pad 70, occluder 62, door support post 42 and pump door 126. For clarity, not all structures of the pump 10 or cassette 14 are shown. The pump door 126 attaches to the pump 10 via a hinge 130 on one side of the pump and door and with a mating latch or catch 134 and receptacle 138 on the other side of the pump and door. The door 126 has a projection 142 formed thereon. The projection 142 has an engagement surface 146 with a curved lower portion 150 which curves away from the engagement surface towards the bottom thereof. The engagement surface 146 contacts the back side 154 of the actuator pad 70 opposite the actuation channel 110. The back side 154 of the actuator pad 70 has a curved upper portion 158.

When the door is closed, the engagement surface 146 contacts the back side 154 of the actuator pad 70 and pushes the actuator pad 70 into the occluder 62 and pump tubing 26 in the manner discussed above to open a flow path 98 past the occluder. Initially, the curved lower portion 150 of the engagement surface 146 contacts the curved upper portion 158 of the back side 154 of the actuator pad 70 and the angular relationship therebetween causes the actuator pad 70 to move sideways as the projection 142 moves down.

Figure 15:
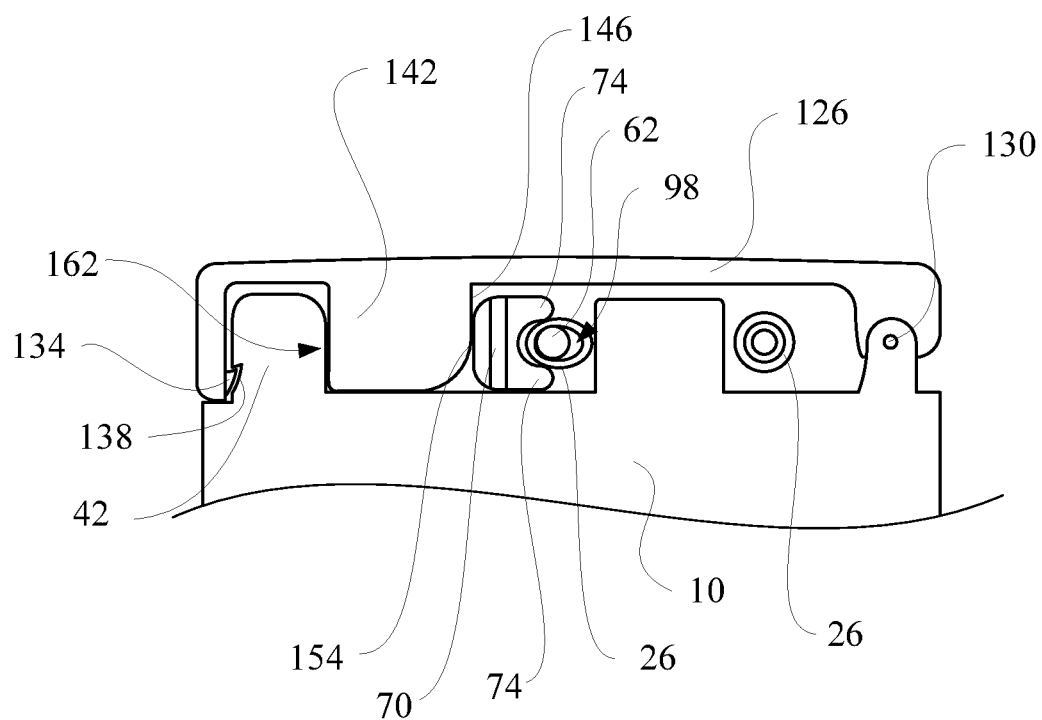

Once the pump door 126 is closed, as is shown in FIG. 15, the flat, vertical portion of the projection contact surface 146 and of the back side 154 of the actuator pad 70 are in contact, eliminating any tendency of the actuator pad 70 to push the door open. The door support post 42 contacts the side of the projection 142 which is opposite the actuator pad 70 and prevents the actuator pad 70 from bending the door and pushing the projection 142 horizontally away from the actuator pad 70.

Figure 16:
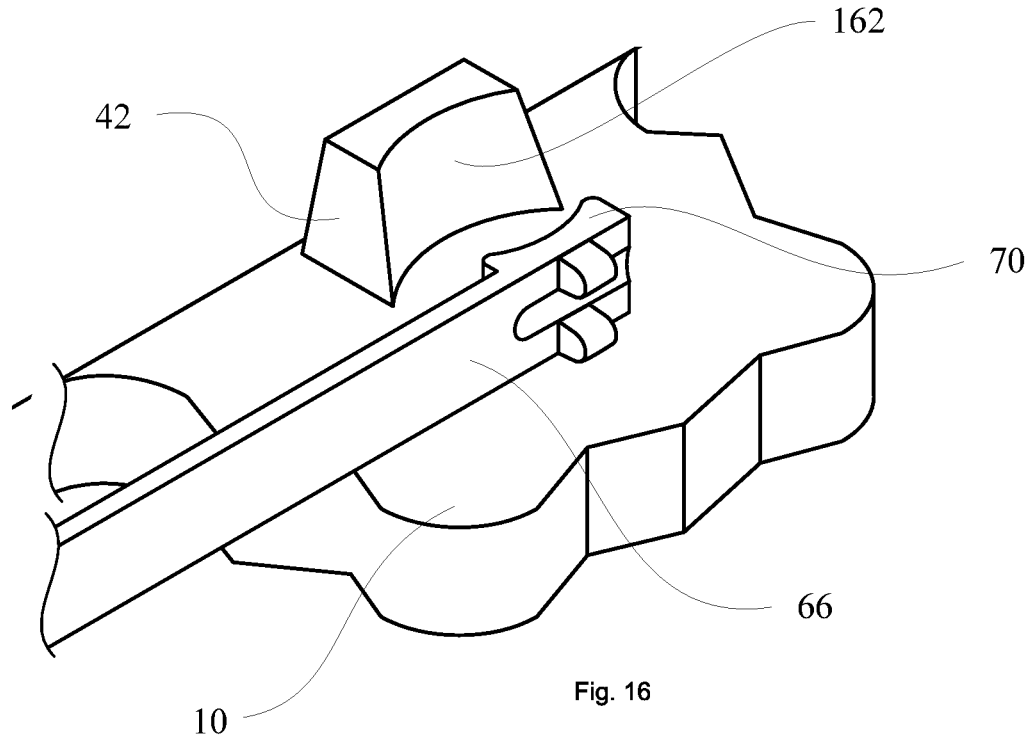
FIGS. 16 and 17 show partial perspective views of the pump and cassette.
Figure 17:
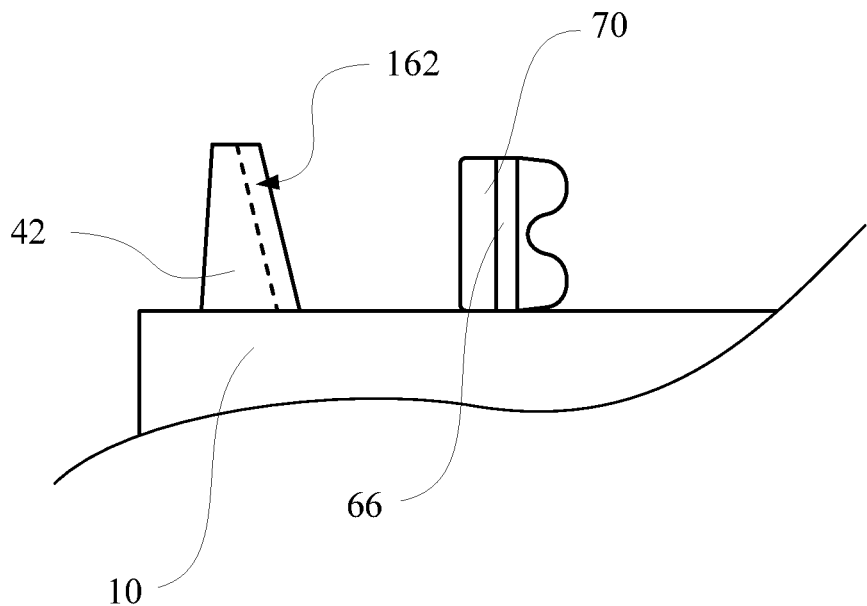

FIGS. 16 and 17 show partial perspective views of the pump 10 and cassette 14, highlighting additional details of the door support post 42. For clarity, many structures of the pump 10 and cassette 14 are not shown. The door support post 42 is preferably formed with a contact surface 162 which faces towards the actuator pad 70 and which contacts the projection 142 as discussed previously. The contact surface 162 is curved side to side as shown so as to center the projection 142 over the contact surface 162 and thereby increase the reliability of creating a flow passage 98 between the occluder 62 and pump tubing 26. The contact surface 162 is also disposed at an angle relative to the pump 10 such that the top of contact surface is farther away from the actuation pad 70 than the bottom of the contact surface. Thus, the contact surface 162 may be disposed at an angle of about 10 to 20 degrees from perpendicular.

Disposing the contact surface 162 at an angle off of perpendicular causes the projection 142 to move inwardly towards the actuation pad 70 as the door 126 is being closed and thereby increases the amount by which the actuation pad 70 may be displaced sideways while simultaneously reducing the likelihood that the door support post 42, projection 142 and actuation pad 70 bind and malfunction while closing the door. Thus, sloping the contact surface 162 results in a more reliable and better functioning system for opening a flow passage past the occluder 62 while simultaneously allowing a larger flow passage to be opened.

It will be appreciated that the present invention may include various features discussed above. For example, an in-line occluder in accordance with one aspect of the invention may include: a flexible tubing having a bore; an occluder disposed in the bore, the occlude having: a body; an occluder, the occluder having a round cross-section and engaging the bore of the tubing to seal against the tubing and prevent flow past the tubing; and a stem connecting the body to the occluder, the stem having a 'T' shaped cross section. The occlude may also include: the stem having a side wall disposed along a side of the stem and a center web attached to the middle of the side wall and extending perpendicular thereto towards an opposite side of the stem; the body having a longitudinal bore extending along the length thereof and a lateral bore extending laterally through and end of the body adjacent the stem; the lateral bore extends generally perpendicular to the center web; a configuration such that fluid flows between the occluder and the tubing, around the center web, and through the body; an actuator pad disposed adjacent the occlude such that the actuator pad presses inwardly on an outer surface of the tubing on one side of the tubing to open a flow passage between the occluder and an opposite side of the tubing; the actuator pad having two projections having curved ends and an actuation channel disposed between the two projections, and wherein the actuator pad engages the tubing between the two projections and presses the tubing and occluder towards the actuation channel; the actuation channel tapering such that a bottom of the channel is narrower than a top of the channel; the two projections having a radius of curvature approximately equal to the radius of the occluder, and the actuation channel having a width approximately equal to the diameter of the occlude; the actuator pad being connected to the occlude; a pump having a pump door such that the occluder and actuator pad are mounted in the pump and the pump door engages the actuator pad to press the actuator pad against the tubing to open a flow channel past the occlude; and/or a projection on the pump door moves in a first direction when the door is closed and wherein the projection engages the actuator pad and presses the actuator pad in a second direction perpendicular to the first direction to thereby press the actuator pad against the tubing; or combinations thereof.

An occluder system of the present invention may include; a flexible tubing having a lumen; an occluder having: a body; a stem having a first end and a second end, the first end being attached to the body; and an occluder attached to the second end of the stem and spaced apart from the body, the occluder being disposed in the lumen of the tube and having a round cross-section with a diameter greater than the diameter of the lumen; an actuator pad, the actuator pad having: two projections; and an actuation channel disposed between the two projections; and wherein the actuation pad selectively engages the tubing on one side of the tubing to create a flow passage between the occluder and an opposite side of the tubing.

The occluder system of the previous paragraph may also include: the two projections having curved ends; the two projections each having a radius of curvature which is approximately equal to the radius of the occlude; the actuation channel having a width approximately equal to the diameter of the occlude; the actuation channel tapering such that a top of the action channel is wider than a bottom of the actuation channel; a top portion of the actuation channel transitioning into the curved ends such that the curved ends curve away from the actuation channel; the actuation channel having a rounded bottom; the actuator pad being movable towards the occluder to engage the tube and open a flow channel between the occluder and the tube; the actuator pad being attached to the occluder and is pivotable towards the occlude; the actuator pad having a recessed tip portion adjacent the projections such that the tip portion contacts the tube to displace the tube laterally when the actuator pad engages the tube to open a flow passage; the actuation channel being tapered so as to be narrower at the bottom; and/or the actuation channel tapering between 5 and 20 degrees; or combinations thereof.

There is thus disclosed an improved anti free-flow occluder and actuator pad. It will be appreciated that numerous changes may be made to the present invention without departing from the scope of the claims.

What is claimed is:

1. An in-line occluder comprising:
a flexible tubing having a bore;
an occluder disposed in the bore, the occluder comprising:
a body;
an occluding portion, the occluding portion having a round cross-section and engaging the bore of the tubing to seal against the tubing and prevent flow past the tubing; and
a stem connecting the body to the occluding portion, the stem having a 'T' shaped cross section.

2. The occluder of claim 1, wherein the stem comprises a side wall disposed along a side of the stem and a center web attached to the middle of the side wall and extending perpendicular thereto towards an opposite side of the stem.

3. The occluder of claim 2, wherein the body comprises a longitudinal bore extending along the length thereof and a lateral bore extending laterally through an end of the body adjacent the stem.

4. The occluder of claim 3, wherein the lateral bore extends generally perpendicular to the center web.

5. The occluder of claim 3, wherein fluid flows between the occluding portion and the tubing, around the center web, and through the body.

6. A system comprising the occluder of claim 2, and further comprising an actuator pad disposed adjacent the occluder, and wherein the actuator pad presses inwardly on an outer surface of the tubing on one side of the tubing to open a flow passage between the occluding portion and an opposite side of the tubing.

7. The system of claim 6, wherein the actuator pad comprises two projections having curved ends and an actuation channel disposed between the two projections, and wherein the actuator pad engages the tubing between the two projections and presses the tubing and the occluding portion towards the actuation channel.

8. The system of claim 7, wherein the actuation channel tapers such that a bottom of the channel is narrower than a top of the channel.

9. The system of claim 7, wherein the two projections have a radius of curvature approximately equal to the radius of the occluding portion, and wherein the actuation channel has a width approximately equal to the diameter of the occluding portion.

10. The system of claim 6, wherein the actuator pad is connected to the occluder.

11. The system of claim 6, further comprising a pump having a pump door, wherein the occluder and actuator pad are mounted in the pump, and wherein the pump door engages the actuator pad to press the actuator pad against the tubing to open a flow channel past the occluding portion of the occluder.

12. The system of claim 11, wherein a projection on the pump door moves in a first direction when the door is closed and wherein the projection engages the actuator pad and presses the actuator pad in a second direction perpendicular to the first direction to thereby press the actuator pad against the tubing.

13. An occluder system comprising:
a flexible tubing having a lumen;
an occluder comprising:
  a body;
  a stem having a first end and a second end, the first end being attached to the body; and
  an occluding portion attached to the second end of the stem and spaced apart from the body, the occluding portion being disposed in the lumen of the tube and having a round cross-section with a diameter greater than the diameter of the lumen;
an actuator pad, the actuator pad comprising:
  two projections; and
  an actuation channel disposed between the two projections; and
wherein the actuation pad selectively engages the tubing on one side of the tubing to create a flow passage between the occluding portion and an opposite side of the tubing.

14. The system of claim 13, wherein the two projections have curved ends.

15. The system of claim 14, wherein the two projections each have a radius of curvature which is approximately equal to the radius of the occluding portion.

16. The system of claim 13, wherein the actuation channel has a width approximately equal to the diameter of the occluding portion.

17. The system of claim 13, wherein the actuation channel tapers such that a top of the actuation channel is wider than a bottom of the actuation channel.

18. The system of claim 13, wherein a top portion of the actuation channel transitions into the curved ends such that the curved ends curve away from the actuation channel.

19. The system of claim 13, wherein the actuation channel has a rounded bottom.

20. The system of claim 13, wherein the actuator pad is movable towards the occluding portion to engage the tube and open a flow channel between the occluding portion and the tube.

21. The system of claim 13, wherein the actuator pad is attached to the occluder and is pivotable towards the occluding portion.

22. The system of claim 13, wherein the actuator pad further comprises a recessed tip portion adjacent the projections, and wherein the tip portion contacts the tube to displace the tube laterally when the actuator pad engages the tube to open a flow passage.

23. The system of claim 13, wherein the actuation channel is tapered so as to be narrower at the bottom.

24. The system of claim 23, wherein the actuation channel tapers between 5 and 20 degrees.

* * * * *